(12) United States Patent
Harris

(10) Patent No.: US 6,248,370 B1
(45) Date of Patent: Jun. 19, 2001

(54) SKIN TREATMENT AND METHODS

(76) Inventor: Leroy Harris, 3026 A1/2 Rd., Grand Junction, CO (US) 81503

(*) Notice: Subject to any disclaimer, the term of this patent is extended or adjusted under 35 U.S.C. 154(b) by 0 days.

(21) Appl. No.: 09/119,218

(22) Filed: Jul. 20, 1998

Related U.S. Application Data

(60) Provisional application No. 60/053,669, filed on Jul. 24, 1997.

(51) Int. Cl.$^7$ ............................ A61K 33/32; A61K 33/24
(52) U.S. Cl. ........................... 424/641; 424/642; 424/650; 424/401; 424/404; 424/488; 424/49; 424/52; 424/70.1; 424/70.8
(58) Field of Search ..................................... 424/401, 404, 424/488, 49, 52, 70.1, 70.8, 641, 642, 650

(56) References Cited

U.S. PATENT DOCUMENTS

| | | |
|---|---|---|
| 5,256,396 | 10/1993 | Piechota, Jr. . |
| 5,382,431 | 1/1995 | Pickart . |
| 5,858,993 | 1/1999 | Pickart . |
| 5,866,168 * | 2/1999 | De Lacharriere .................... 424/639 |
| 5,876,922 | 3/1999 | Orth et al. . |

* cited by examiner

Primary Examiner—Dwayne C. Jones
Assistant Examiner—C. Delacroix-Muirheid
(74) Attorney, Agent, or Firm—Pittenger & Smith, P.C.

(57) ABSTRACT

Medicinal compositions for the topical treatment of skin diseases or conditions which contain a combination of a zinc compound and tin compound in an inert carrier, liquid or solid. Optionally, the composition can include a small amount of a selenium compound as a part of the active ingredient combination.

6 Claims, No Drawings

SKIN TREATMENT AND METHODS

This application claims the benefit of U.S. Provisional Application No. 60/053,669, filed Jul. 24, 1997.

BACKGROUND OF THE INVENTION

This invention relates to medicinal compositions for treatment of the skin and methods therefor.

Zinc compounds have been used in the past for treating the skin in the form of powders and ointments. It has been found that the combination of a zinc compound and a tin compound (stannous compound) is very effective for treating diseases of the skin such as psoriasis, acne, melanism, lupus, and other skin disorders.

SUMMARY OF THE INVENTION

More particularly, the medicinal compositions of the present invention include the combination of a zinc compound and a tin compound which is highly effective for the treatment of diseases of the skin. The compositions contain only a very small percentage of the zinc compound and tin compound, the balance of the composition being an inert carrier or a delivery system.

In a second embodiment of the medicinal compositions of the present invention, there is included a small amount of selenium compound such as selenium sulfide (usually a mixture of the sulfides) along with the combination of a zinc compound and a tin compound.

DETAILED DESCRIPTION OF THE INVENTION

In the practice of the present invention, a combination of the zinc compound and tin compound, and, optionally, selenium compound, is applied to the skin in an inert carrier or delivery system which may be either a solid or a liquid. Suitable solid inert carriers in the form of a powder for dusting include talc, kaolin, clay, calcium carbonate, cellulose, corn starch and the like. Suitable liquid inert carriers include glycerol, petrolatum, light mineral oil, lanolin, vegetable oils such as olive, cotton seed and sesame oil, skin care creams such as baby creams, cleaning creams and cold creams, hand and skin lotions, hair lotions and shampoos, and the like. Some liquid compositions can be applied by spraying by aerosol or pump.

The percentage of active ingredient (combination of the zinc compound and tin compound) in the compositions of the present invention can be varied. It is, however, necessary that the active ingredient constitute a proportion of the composition such that an effective amount (dosage) will be obtained. The active ingredient is preferably used in a percentage of at least about 0.005 percent of the weight of the composition. The most effective concentration of the active ingredient in the composition can be determined by routine testing giving due consideration to the skin disease being treated and the condition thereof.

The compositions of the present invention are effective against skin diseases or conditions such as psoriasis, acne, eczema, cold sore, athlete's foot, abrasions, dandruff, and the like. One or more topical applications of the compositions of the present invention can be applied to cure such skin disease or condition depending upon the severity thereof.

The zinc compound and the tin compound are used in substantially equal proportion by weight in the preferred embodiment of the compositions of the present invention as the active ingredient. Larger or smaller amounts of each compound can be used in the combination; however, neither compound is present in simply a trace amount of the combination. The most advantageous proportion of the two compounds can be determined by those of ordinary skill in the art using routine testing.

The zinc compound can be selected from zinc salts such as zinc sulfate hydrates, zinc esters such as zinc stearate, zinc propionate, zinc salicylate, and the like.

The tin compound can be selected from tin halides such as tin diflouride (stannous fluoride), and the like.

Similarly, as a part of the active ingredient, optionally, there can be included a small amount of selenium compound along with the zinc compound and tin compound. The amount of or percentage of the selenium compound such as selenium sulfide(s) can be varied. It is generally a lesser amount than either the zinc compound or tin compound. This composition is useful for dry skin disorders such as dandruff and other skin diseases.

EXAMPLE 1

A liquid composition containing:

| | |
|---|---|
| Zinc sulfate monohydrate | 1.9 grams |
| Stannous fluoride | 1.9 grams |
| Glycerol | 450.2 grams | is heated to about 150 degrees F. with stirring for about 4 hours. After cooling to room temperature, the composition is applied lightly to a cold sore with excellent results.

EXAMPLE 2

A solid composition containing:

| | |
|---|---|
| Zinc sulfate monohydrate | 2.0 grams |
| Stannous fluoride | 2.0 grams |
| Talcum powder | 450.0 grams | is thoroughly blended. This composition is an excellent treatment for athlete's foot using only a few dustings. The composition of Example 1 gives excellent results on athlete's foot also.

EXAMPLE 3

A shampoo containing:

| | |
|---|---|
| Sodium lauryl ether sulfate | 200.0 grams |
| Water | 200.0 grams |
| Zinc sulfate monohydrate | 1.2 grams |
| Stannus fluoride | 1.1 grams |
| Selenium sulfides | 0.8 grams | is prepared with mild heating. The shampoo is very effective against dandruff and sores (lesions) on the scalp.

What is claimed is:

1. A medicinal composition for the treatment of skin disorders consisting essentially of the following proportions by weight of components:

1.9 g. zinc sulfate monohydrate;

1.9 g. stannous fluoride; and 450.2 g. glycerol.

2. A medicinal composition for the treatment of athlete's foot consisting essentially of the following proportions by weight of components:

2.0 g. zinc sulfate monohydrate;

2.0 g. stannous fluoride; and 450.0 g. talcum powder.

3. A shampoo consisting essentially of the following proportions by weight of components:

1.2 g. zinc sulfate monohydrate;

1.1 g. stannous fluoride;

0.8 g. selenium sulfide;

200.0 g. sodium lauryl ether sulfate; and 200.0 g. water.

4. A method of treating skin disorders comprising applying to the skin an effective amount of a medicinal composition consisting essentially of the following proportions by weight of components:

1.98 g. zinc sulfate monohydrate;

1.98 g. stannous fluoride; and 450.28 g. glycerol.

5. A method of treating athlete's foot comprising dusting the foot with a medicinal composition consisting essentially of the following proportions by weight of components:

2.0 g. zinc sulfate monohydrate;

2.0 g. stannous fluoride; and 450.0 g. talcum powder.

6. A method of treating scalp disorders comprising shampooing the scalp with a shampoo consisting essentially of the following proportions by weight of components:

1.2 g. zinc sulfate monohydrate; 1.1 g. stannous fluoride;

0.8 g. selenium sulfide;

200.0 g. sodium lauryl ether sulfate; and 200.0 g. water.

* * * * *